United States Patent [19]

Euvrard

[11] Patent Number: 5,431,565
[45] Date of Patent: Jul. 11, 1995

[54] VIBRATING SCALER FOR DENTISTRY

[75] Inventor: Hubert Euvrard, Geneuille, France

[73] Assignee: Micro Mega SA, Besancon, France

[21] Appl. No.: 43,668

[22] Filed: Apr. 6, 1993

[30] Foreign Application Priority Data

Apr. 6, 1992 [FR] France ............................ 92 04328

[51] Int. Cl.6 ................................................ A61C 1/07
[52] U.S. Cl. ......................................... 433/119; 433/86
[58] Field of Search ............... 433/118, 119, 120, 122, 433/123, 86

[56] References Cited

U.S. PATENT DOCUMENTS

| | | | |
|---|---|---|---|
| 3,076,904 | 2/1963 | Kleesattel et al. | 433/118 |
| 4,453,919 | 6/1984 | Takeshita | 433/120 |

*Primary Examiner*—Cary E. O'Connor
*Attorney, Agent, or Firm*—Weiser & Associates

[57] ABSTRACT

Scaler consisting of a body comprising at its proximal end a device of known type for rapid connection to the lead of the dental unit, and leaving its distal end a scaling curette, and at its inside a vibration-generation device, characterized in that the scaling curette forms an integral part of the vibration-transmission device, and in that it cannot be detached therefrom.

13 Claims, 1 Drawing Sheet

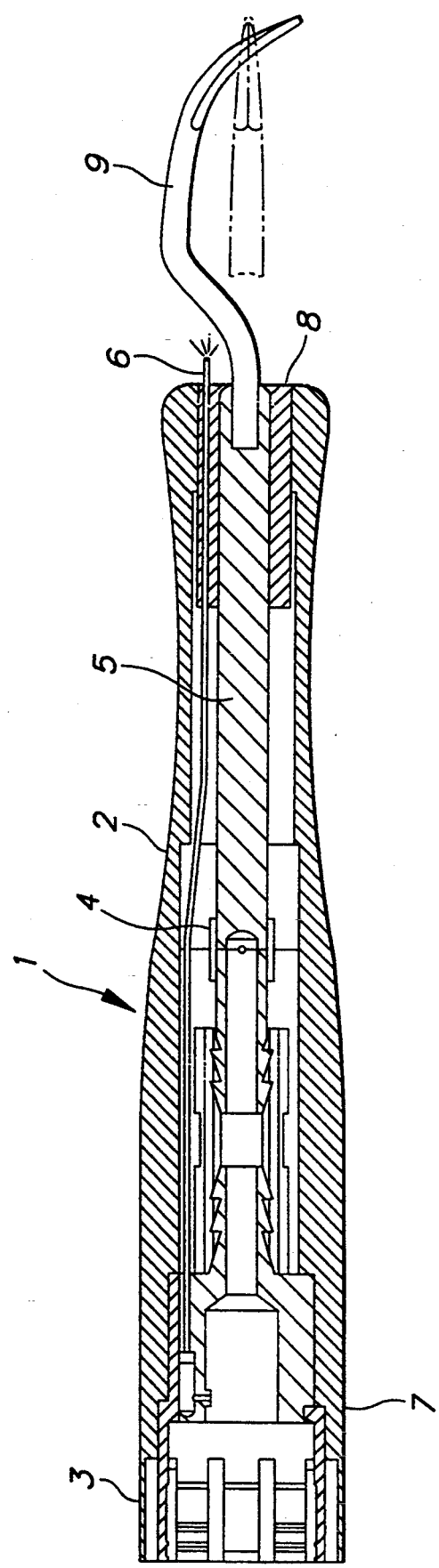

VIBRATING SCALER FOR DENTISTRY

BACKGROUND OF THE INVENTION

The present invention relates to the field of mechanized scalers used in dentistry, and more particularly to the field of vibrating scalers whose vibration is for example obtained by means of air-driven devices.

Multiple embodiments/modes of air-driven scalers are currently known, for example those described in U.S. Pat. No. 3,811,190 and U.S. Pat. No. Re. 29687 as well as FR 2,525,893 and FR 2,505,172.

In general, these scalers are expensive products, and, although devices for rapid connection to the leads of the dental unit have been developed, they require on the part of the dentist, when he wishes to change the curette depending on the work to be performed, detaching of the curette which is most often fixed by screwing, and its replacement with the one which is suitable for the next work.

A significant loss of time results. Furthermore, the detachment and re-attachment of the curettes presents non-negligible risks of cross-contamination, for example by the risk of the dentist or his assistant pricking themselves when unscrewing the curette.

SUMMARY OF THE INVENTION

The object of the present invention is to provide a scaler or a set of scalers which make it possible to solve the aforementioned problems, in particular by removing the requirement for detaching the curettes, and whose economical production allows the practitioner to have available a set of scalers, each provided with a curette corresponding to the work to be carried out.

More precisely, the invention relates to a scaler consisting of a body comprising at its proximal end a device of known type for rapid connection to the lead of the dental unit, and at its distal end comprising a scaling curette, and at its inside a vibration-generation device, characterized in that the scaling curette forms an integral part of the vibration-transmission device, and in that it cannot be detached.

BRIEF DESCRIPTION OF THE DRAWING

The invention will be better understood with the aid of the description given hereinbelow of one embodiment, given by way of non-limiting example, and with reference to the single attached figure which is a side elevation in longitudinal section of a scaler according to the invention.

The elements of the scaler which belong to the state of the art will not be described in detail.

The scaler, generally referred to by (1), comprises an elongate body (2) used as a handle for holding by the practitioner. It is connected at its proximal end (3) in a known manner, by a rapid-connection device, to the supply lead of the dental unit.

It comprises on the inside a vibration-generation device (4), of conventional type.

According to an essential characteristic of the invention, the device (4) is connected in a manner which cannot be detached by the user, to the scaling curette (9) located at the distal part of the body (1).

The curette will be connected to the device (4) by a vibration-transmission member (5), with which it will form a preferably monobloc structure. It may be supported thereon for example by welding or brazing.

Thus, each scaler may be fitted with a specific curette. It is therefore possible to have a set of scalers according to the invention, each having a curette specific to each type of work to be carried out. According to a variant embodiment, the curette will be driven into a bore made at the front part of the transmission member (5).

Preferably, the assembly constituted by the vibration device, the vibration-transmission device, the curette as well as the suspensions, the rapid-connection device and the device (6) for irrigating the curette will be introduced entirely assembled into the body (2) through its proximal end.

Holding will be obtained for example by driving the rapid-connection device inside the body in a housing (7) situated at its proximal end.

The act of producing the fixing by welding, for example using ultrasound, would not depart from the scope of the invention.

In order to limit the cost price, the connection device and/or the body (2) will be made from a plastic which is compatible with the various constraints of use and of possible sterilization.

As an advantageous variant, the body (2) will be made from an elastomer, and the front suspension shaft (8) will be made in a single piece with the said body.

I claim:

1. A scaler comprising an elongate body, a device at a proximal end of the body for rapid connection to a supply lead of a dental unit, a scaling curette at a distal end of the body, a vibration-generation device inside the body and a vibration-transmission member integral with the undetachably connected to the curette, wherein the rapid-connection device, the vibration-generation device, the vibration-transmission member and the curette together constitute an assembly, wherein the body has an internal housing for receiving the assembly, and wherein the assembly may be introduced entirely assembled into the body through its proximal end.

2. The scaler of claim 1 which further comprises, as a part of the assembly, a device for irrigating the curette.

3. The scaler of claim 1 wherein the curette and the vibration-transmission member form a monobloc structure.

4. The scaler of claim 1 wherein the curette is attached to the vibration-transmission member by welding.

5. The scaler of claim 1 wherein the curette is attached to the vibration-transmission member by brazing.

6. The scaler of claim 1 wherein the curette is driven into a bore formed in distal portions of the vibration-transmission member.

7. The scaler of claim 1 wherein the assembly is held integral with the body by driving the rapid-connection device into a housing situated at the proximal end of the body.

8. The scaler of claim 1 wherein the assembly is fixed by welding the rapid-connection device into the body.

9. The scaler of claim 8 wherein the welding is by ultrasound.

10. The scaler of claim 1 wherein the rapid-connection device is made from plastic.

11. The scaler of claim 1 wherein the body is made from plastic.

12. The scaler of claim 1 wherein the body is made from an elastomeric material.

13. The scaler of claim 12 which further comprises, as a part of the body, a front suspension shaft to receive and hold the assembly.

* * * * *